United States Patent
Kolberg et al.

(10) Patent No.: US 7,110,828 B2
(45) Date of Patent: Sep. 19, 2006

(54) INTRAVASCULAR ELECTRODE LINE

(75) Inventors: Gernot Kolberg, Berlin (DE); Max Schaldach, deceased, late of Erlangen (DE); by Max Schaldach, Jr., legal representative, Berlin (DE)

(73) Assignee: Biotronik Mess-und Therapiegeraete GmbH & Co., Berlin (DE)

( * ) Notice: Subject to any disclaimer, the term of this patent is extended or adjusted under 35 U.S.C. 154(b) by 483 days.

(21) Appl. No.: 10/099,550

(22) Filed: Mar. 15, 2002

(65) Prior Publication Data
US 2002/0169492 A1 Nov. 14, 2002

(30) Foreign Application Priority Data
Mar. 21, 2001 (DE) ............... 101 14 725

(51) Int. Cl.
*A61N 1/05* (2006.01)
(52) U.S. Cl. ............... 607/126; 607/127
(58) Field of Classification Search ............... 607/119, 607/122, 123, 125–128
See application file for complete search history.

(56) References Cited

U.S. PATENT DOCUMENTS

| | | | |
|---|---|---|---|
| 4,374,527 A | 2/1983 | Iversen | |
| 4,414,986 A * | 11/1983 | Dickhudt et al. | 607/117 |
| 5,057,092 A * | 10/1991 | Webster, Jr. | 600/435 |
| 5,170,802 A | 12/1992 | Mehra | |
| 5,387,233 A | 2/1995 | Alferness | |
| 5,423,884 A | 6/1995 | Nyman | |
| 5,476,498 A * | 12/1995 | Ayers | 607/122 |
| 5,741,319 A | 4/1998 | Woloszko | |
| 5,876,429 A | 3/1999 | Schroeppel | |
| 5,922,014 A | 7/1999 | Warman | |
| 5,925,073 A | 7/1999 | Chastain | |
| 5,995,876 A | 11/1999 | Kruse | |
| 6,033,397 A | 3/2000 | Laufer | |
| 6,097,986 A | 8/2000 | Janke | |
| 6,129,750 A | 10/2000 | Tockman | |
| 6,161,029 A | 12/2000 | Spreigl | |
| 6,556,874 B1 * | 4/2003 | Audoglio | 607/126 |

* cited by examiner

Primary Examiner—George R. Evanisko
(74) Attorney, Agent, or Firm—Hahn Loeser & Parks LLP; John J. Cunniff

(57) ABSTRACT

An intravascular electrode line is provided with a shaping suitable for fixing in a blood vessel. The shaping is three-dimensional and has line portions enclosing an elongated hollow space, with a pitch direction that is different in relation to the longitudinal direction of the hollow space.

10 Claims, 4 Drawing Sheets

INTRAVASCULAR ELECTRODE LINE

The invention concerns an intravascular electrode line of a configuration suitable for fixing in a blood vessel.

BACKGROUND OF THE ART

Electrode lines or leads, which for example are inserted into blood vessels or through blood vessels into a chamber of a heart, are basically known. Such electrode lines generally carry electrodes which serve to deliver electrical pulses to body tissue surrounding the electrode line or lead, or to receive electrical signals from the body tissue. For example, stimulation electrodes for cardiac pacemakers are known.

It is also known for electrode lines to be deformed two-dimensionally, for example in a coil form, so that the outer arcs of the electrode line formed as a coil bear against the walls of a vessel and thus provide the electrode line with a hold in the vessel, as is shown for example in U.S. Pat. Nos. 4,374,527, 5,922,014 and 5,925,073. An electrode line which is three-dimensionally deformed in such a way that it provides a hold for the line in the atrium of a heart is known for example from U.S. Pat. No. 5,995,876. In that case the electrode line is shaped in such a way that electrodes bear against the myocardium in the region of the atrium.

In addition, U.S. Pat. Nos. 5,387,233 and 6,129,750 disclose electrode lines which are wound in a helical configuration and which are adapted for insertion into a blood vessel, more specifically into the coronary sinus, and bear with the turns of the helix against the vessel walls of the coronary sinus.

The present invention primarily relates to intravascular electrode lines, that is to say electrode lines for elongate blood vessels such as arteries or veins. In contrast to for example heart chambers with their bulging recess configurations which provide a hold for a line, the task involved in providing a hold for electrode lines in elongate blood vessels is a different one. The walls of the blood vessels should as far as possible not be damaged, and in addition the blood vessel should still remain capable of passing blood and not blocked by the electrode line.

Taking the above-depicted state of the art as its starting point, the object of the invention is to provide an intravascular electrode line of an alternative configuration affording a hold therefor.

SUMMARY OF THE INVENTION

In accordance with the invention that object is attained by an electrode line or medical lead of the kind set forth in the opening part of this specification, which involyes a three-dimensional shaping at least in a portion and there includes an elongate hollow space, wherein the lead has at least two line (sub)-portions with a different pitch direction in respect of the longitudinal direction of the hollow space, or a different winding direction of the lead.

The electrode lines known from U.S. Pat. Nos. 5,387,233 and 6,129,750, like the electrode line according to the invention, are also shaped three-dimensionally, namely in a helical configuration, wherein the helix respectively formed by the electrode line encloses a hollow space. In those known electrode lines, the electrode line in the region of the helix involves throughout the same pitch direction or the same winding direction. The electrode line according to the invention differs from that state of the art in that the pitch direction or winding direction of the electrode line in the three-dimensionally deformed condition changes at least once. That affords in particular the manufacturing advantages which will be discussed in greater detail hereinafter. In addition torsional effects which occur in the known electrode lines which are deformed in a helical configuration upon stretching or upsetting of the helix portion can be specifically compensated.

A very simple and therefore preferred electrode line has two line portions shaped in a helix-like manner, involving opposite pitches. In the case of such an electrode line, the different pitch direction thus arises out of the opposite direction of rotation of the underlying helix. Such an electrode line can be easily manufactured by firstly being shaped in the manner of a triangle which is open at one side. Then, the triangle formed in that way is wound around a cylinder. That gives an electrode line which is simple to produce and in which torsional forces upon stretching or upsetting of the deformed line portion are compensated to the best possible extent.

In an alternative preferred embodiment the development of the electrode line which includes a hollow cylinder is not triangular but Ω-shaped. An essential feature of that Ω-shape is a kind of negative pitch or undercut, as is described in the specific description hereinafter with reference to the drawing. That negative pitch or undercut configuration provides that the diameter of the enclosed hollow space increases so that the correspondingly shaped electrode line is wedged when subjected to a tensile loading in a blood vessel in the form of a hollow cylinder as, when a tensile loading is applied, the electrode line presses more firmly against the wall of the vessel. The fixing of the electrode line thus becomes firmer when a tensile loading is applied. If in contrast the pitch of the pre-shaped line portions is only positive—irrespective of the direction of rotation of the underlying helix—the enclosed hollow space decreases when a tensile loading is involved so that the wedging action does not occur. Besides arising out of the direction of rotation of the respective underlying helix, a different pitch direction can thus alternatively or additionally also arise out of the fact that the line portions enclosing the hollow space also have portions in which the component in respect of extent of the electrode line, in parallel relationship with the longitudinal direction of the enclosed hollow space, has different signs, accordingly a negative or a positive pitch.

Further advantageous alternative configurations concern introduction of the electrode line variants into a blood vessel. That is made easier by virtue of the fact that the electrode line is stretched as far as possible in the introduction operation and assumes its three-dimensional configuration only when it has reached its destination. An alternative configuration which advantageously permits that to be done involves a three-dimensionally pre-shaped electrode line which, by virtue of the introduction of a stiletto into the lumen enclosed by the electrode line, can be so stretched that it is easy to introduce into blood vessels.

In another alternative variant, the electrode line is of a flexurally soft nature and has a lumen. A controllable guide wire for example can be inserted into that lumen in order in that way to be able to targetedly control the electrode line upon introducing it into a blood vessel. When the electrode line has reached the destination, instead of the control wire it is possible to introduce into the lumen for example a three-dimensionally pre-shaped stiletto, for example in the form of a three-dimensionally pre-shaped spring wire. That then imposes its shape on the flexurally soft electrode line.

A further alternative configuration involves an electrode line which has a stiffening coil of elastic material which is formed into a plurality of turns. Provided in the lumen of that electrode line is a chord or fiber or filament which is fixed with its distal end to the electrode line. In that way, applying a pulling force to the fiber gives an upsetting force in the electrode line. The coil is of such a configuration that when a pulling force is applied on the fiber the electrode line flexurally deflects from its longitudinal direction and assumes a predetermined three-dimensional shape. When suitable materials are used, that shape can be fixed so that the electrode line retains the three-dimensional deformation when the pulling force by way of the fiber is relaxed.

Yet another embodiment is distinguished by a memory metal element which for example has a per se known titanium alloy which, when a triggering temperature is exceeded, changes its shape from a first shape to a second shape. That memory metal element is such that its first shape corresponds to a substantially straight electrode line which permits easy insertion of the electrode line while the second shape of the memory metal, after the triggering temperature is exceeded, results in a three-dimensionally deformed electrode line. Advantageously, it is possible to provide a heating element for heating the memory metal element to the triggering temperature if the body temperature is not sufficient to reach the triggering temperature. If the body temperature is sufficient to reach the triggering temperature at which the memory metal changes its shape, it is possible to provide cooling means, alternatively the electrode lines can also be introduced in the cooled condition so that during and after introduction into the blood vessel it slowly warms up and finally reaches the triggering temperature.

Advantageously the electrode line in the region of its three-dimensional shaping carries at least one electrode in such a way that the electrode bears against the wall of a respective blood vessel.

BRIEF DESCRIPTION OF THE DRAWINGS

The invention will now be described in greater detail by means of embodiments with reference to the Figures in which.

DETAILED DESCRIPTION OF THE INVENTION

Figure 1A:
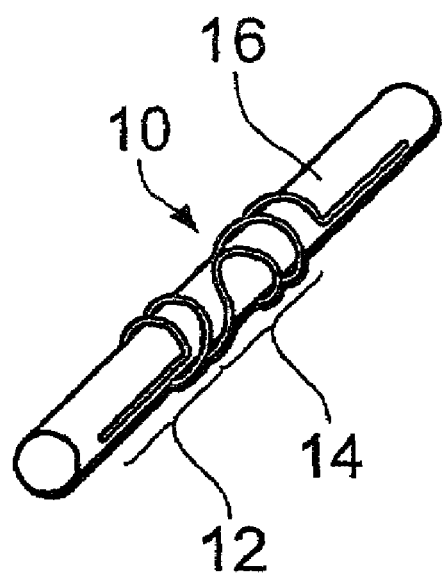
FIGS. 1a and b show a first embodiment of a three-dimensionally deformed electrode line and a sketch showing how this embodiment can be produced, FIGS. 2a and b show an alternative embodiment and a sketch showing how the alternative embodiment can be produced.
Figure 1B:
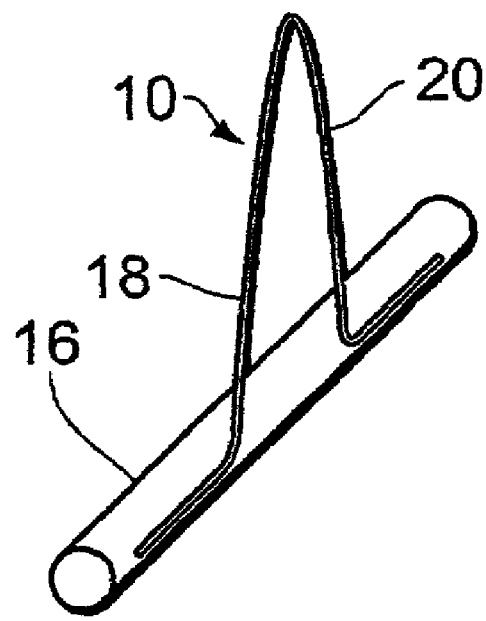
Figure 2A:
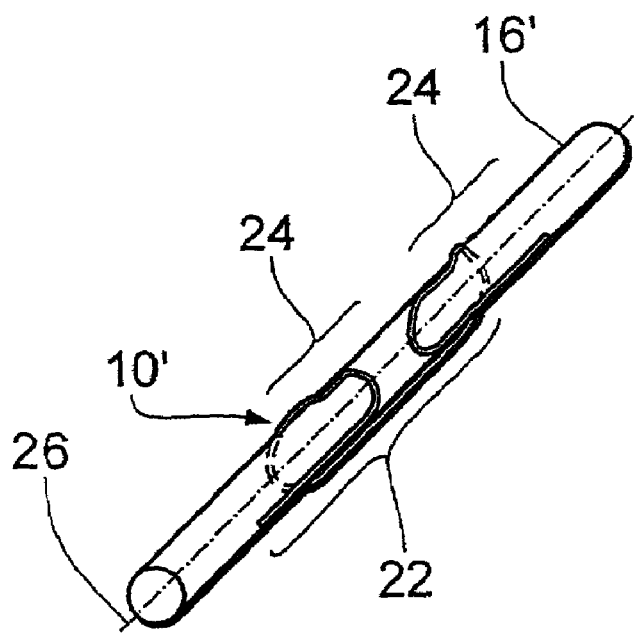

FIGS. 1a and 2a each show in diagrammatic form a three-dimensionally shaped portion of an electrode line 10. In the case of FIG. 1a the three-dimensionally shaped portion is composed of two sub-portions 12 and 14 which are each of a helical configuration and which differ from each other by virtue of the pitch or the winding direction of the helix. The three-dimensionally shaped portion of the electrode line, shown in FIG. 1a, can be produced by the electrode line 10 firstly being shaped in a triangular configuration, as is shown in FIG. 1b. Then the triangularly shaped portion of the electrode line 10 is wound around a cylinder 16, as indicated in FIG. 1b. The two legs of the triangle which are each formed by a respective portion 18 and 20 of the electrode line in that way afford the two sub-portions 12 and 14 of the three-dimensionally shaped electrode line of FIG. 1a.

Figure 2B:
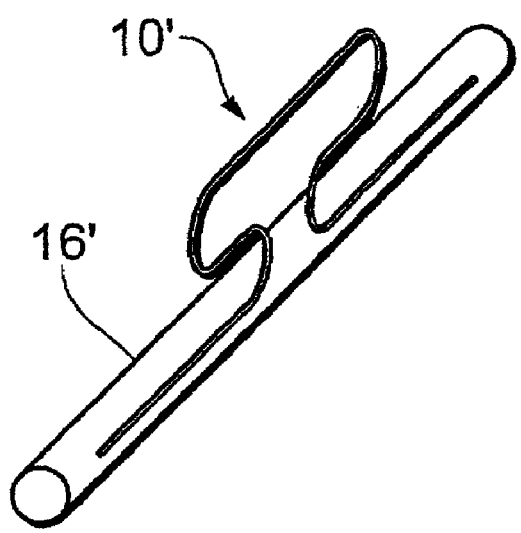

The three-dimensionally shaped electrode portion 22 shown in FIG. 2a can be produced in a similar manner to that described hereinbefore, by a procedure whereby the electrode line 10' is firstly pre-shaped in an Ω-shape, as indicated in FIG. 2b, and the Ω-portion is wound around a cylinder 16'. This provides that the three-dimensionally shaped portion 22 of the electrode line 10' shown in FIG. 2a, in the development of the cylinder enclosed by the line portion, is Ω-shaped. That therefore affords line portions 24 whose components of extent in parallel relationship with a longitudinal axis 26 of the enclosed hollow space 16' involve a different orientation or sign-related direction, from the rest of the line portions. The line portions 24 'go back' and thus have a negative pitch and accordingly afford undercut configurations.

Besides the manufacturing variants illustrated, it is also possible to envisage others. FIGS. 1a and 1b and FIGS. 2a and 2b serve in particular to describe the relationship between the respective three-dimensional shape of the shaped electrode line 10 or 10' respectively and the corresponding flat representation by virtue of developing the cylinder enclosed by the electrode line. The hollow space enclosed by the electrode line in the three-dimensionally shaped portion does not necessarily have to be cylindrical, it can also be in the form of a truncated cone or any other elongate shape, for example a prism shape.

FIGS. 3 through 5 show different embodiments of electrode lines which in the straightened form can be introduced into a respective blood vessel and can assume their three-dimensional shape after insertion.

The electrode line 10 in FIG. 3 includes a sleeve 30 (only indicated in FIG. 3a) and within the sleeve 30 a metal coil 32 and a fiber or filament 34 which is arranged in a lumen enclosed by the metal coil 32 and which at its distal end is connected by way of a connecting plate 36 to the metal coil 32.

Figure 3B:
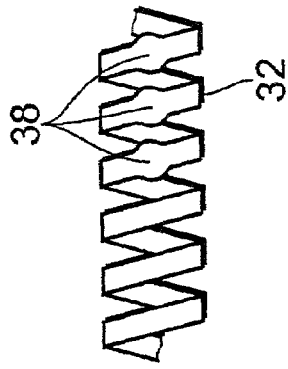
FIGS. 3a through d show an embodiment of an electrode line which is deformable by upsetting a stiffening coil, FIGS. 4a and b show a portion of a flexurally soft electrode line which is deformable by insertion of a pre-shaped stiletto.
Figure 3C:
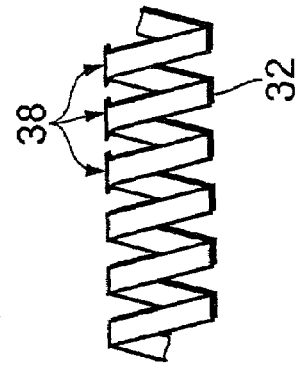
Figure 3D:
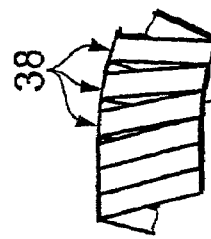
Figure 3A:
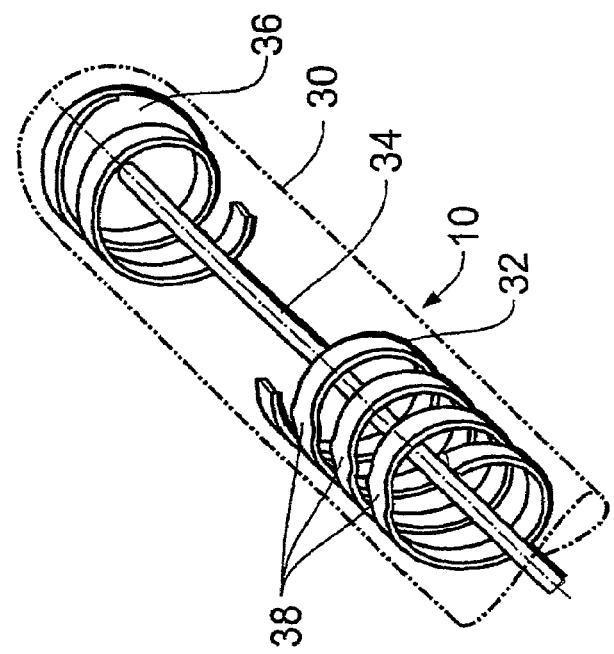

FIG. 3b shows a plan view of a portion of the metal coil 32 and FIG. 3c shows a side view of the portion of the metal coil 32. It will be seen that the individual turns of the metal coil 32 are spaced from each other and that the strip material which constitutes the metal coil 32 is wider at each of the locations 38. By virtue of pulling on the fiber 34 the metal coil 32 is reduced in length until the turns of the metal coil 32 bear against each other; see FIG. 3d. As the strip material of the metal coil 32 is widened at each of the locations 38, the shortened or upset metal coil 32 does not retain its elongatedly straight shape but assumes the flexed condition shown in FIG. 3d. On the basis of the principle shown in FIG. 3, the turns corresponding to the metal coil 32 can be designed in such a way that an electrode line assumes any three-dimensional curvatures by virtue of pulling on a fiber inserted therein. Without a pulling force being applied to the fiber the electrode line is straight and flexurally soft and can be easily introduced into the blood vessel, as indicated in FIG. 3a.

Figure 4B:
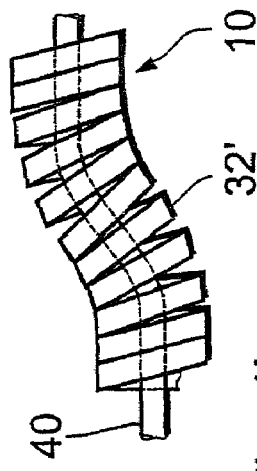
Figure 4A:
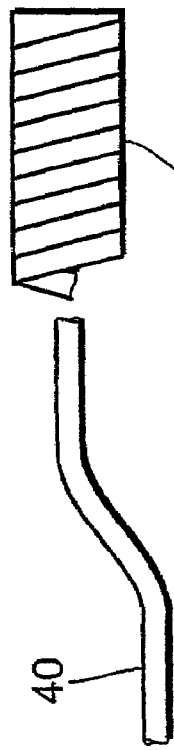

FIGS. 4a and 4b are based on an initially flexurally soft electrode line 10 into which, after placement in a blood vessel, a pre-shaped spring steel wire 40 can be introduced in the manner of a stiletto, as is indicated in FIG. 4a. After introduction of the spring steel wire 40 the electrode line 10 assumes the shape which is predetermined by the spring steel wire 40; see FIG. 4b.

Figure 5B:
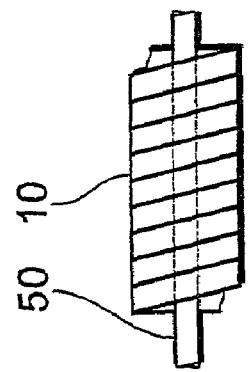
FIGS. 5a through c show a three-dimensionally pre-shaped electrode line which can be straightened by inserting a straightening stiletto.
Figure 5A:
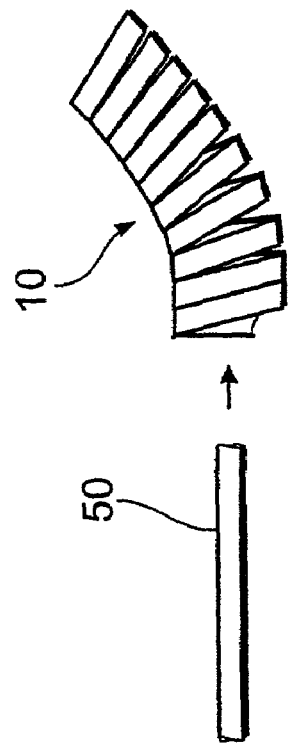
Figure 5C:
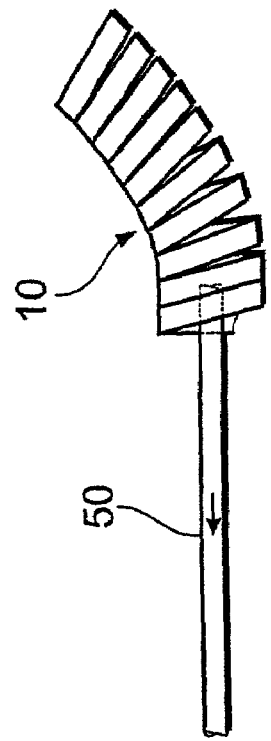

The electrode line 10 shown in FIGS. 5a and b is as such already three-dimensionally pre-shaped and can be straightened by the introduction of a suitably stiff stiletto 50, as is indicated in FIG. 5b. The stiletto 50 can also be moderately bent in order to provide for controlling the end of the electrode line 10. After placement of the electrode line 10 the stiletto 50 is removed again, see FIG. 5c, and the electrode line 10 assumes its originally predetermined, three-dimensional shape. Pre-shaping of the electrode line 10 in FIG. 5 is effected by firstly a wire being bent to correspond to the desired pre-shaping of the electrode line, similarly to the spring steel wire 40 in FIG. 4, and by the metal coil of the electrode line then being pushed on to the pre-shaped wire. Similarly to the situation in FIG. 4, the metal coil assumes the shape of the bent wire. The metal coil together with the bent wire is then heated to incandescence (annealed) so that the structure of the metal coil is changed and the metal coil retains its pre-shaping even without the bent wire. After annealing of the metal coil it can also be quenched, that is to say suddenly cooled, so as to give a spring-elastic metal structure.

What is claimed is:

1. A medical lead comprising at least one electrode and an intravascular electrode line adapted to carry the at least one electrode, the electrode line comprising a shaping suitable for fixing in a blood vessel, wherein the shaping is three-dimensional and comprises first and second coiled line portions connected in series and defining an elongated hollow space, wherein said first and second coiled line portions have different pitch directions in relation to the longitudinal direction of the hollow space, wherein the electrode line is adapted such that the walls of the blood vessels as far as possible should not be damaged and wherein the electrode line is adapted to bear against the walls of a blood vessel in the region of the first and second coiled sections.

2. The medical lead of claim 1, wherein said first and second line portions are shaped helically and which differ from each other by an opposite rotational direction in their pitch direction.

3. The medical lead of claim 1, wherein said first and second coiled line portions comprise two helically shaped line portions which differ from each other by the direction of a component of extent of the electrode line, in parallel relationship with a longitudinal axis of the enclosed hollow space.

4. An intravascular electrode line, comprising a shaping suitable for fixing in a blood vessel, wherein the shaping is three-dimensional and comprises first and second coiled line portions connected in series and enclosing an elongated hollow space, wherein said first and second coiled line portions have different pitch directions in relation to the longitudinal direction of the hollow space, wherein the coiled line portions enclosing a hollow space comprise a wrapped Ω-shape around the hollow space.

5. The medical lead of claim 1, further comprising a lumen within the electrode line adapted for the insertion of a control means, wherein the electrode line is three-dimensionally pre-shaped and can be straightened by the insertion of a stiletto into the lumen.

6. The medical lead of claim 1, further comprising a lumen for the insertion of a control means, wherein the electrode line is flexurally soft and is three-dimensionally deformable by the insertion of a pre-shaped stiletto.

7. The medical lead of claim 1, further comprising a sleeve which encloses a stiffening coil of elastic material which is formed from a plurality of turns and which in turn encloses a lumen, wherein a Fiber is arranged in the lumen of the electrode line and fixed with a distal end of the fiber in such a way that a force can be produced in the electrode line, said force acting in the longitudinal direction of the electrode line and upsetting the electrode line, and wherein the elastic material forming the turns of the coil is shaped in such a way that the electrode line is three-dimensionally deformed when the fiber is tightened and the upsetting force is acting.

8. The medical lead of claim 1, further comprising a memory metal element which changes its shape from a first predetermined shape to a second predetermined shape when a jump temperature is exceeded, wherein the first shape of the memory metal element corresponds to a substantially straight electrode line and the second shape results in a three-dimensionally deformed electrode line.

9. The medical lead of claim 8, further comprising a heating element for heating the memory metal element to the jump temperature.

10. The medical lead of claim 1, wherein said at least one electrode is for receiving and/or delivering electrical signals from or to body tissue surrounding the electrode line, wherein the at least one electrode is positioned in the region of the three-dimensional shaping of the electrode line.

* * * * *